(12) United States Patent
Chou

(10) Patent No.: US 9,198,589 B2
(45) Date of Patent: Dec. 1, 2015

(54) ECG SIGNAL ACQUISITION DEVICE

(75) Inventor: Chang-An Chou, Taipei (TW)

(73) Assignee: MD Biomedical, Inc., Taipei (TW)

( * ) Notice: Subject to any disclaimer, the term of this patent is extended or adjusted under 35 U.S.C. 154(b) by 191 days.

(21) Appl. No.: 13/496,489

(22) PCT Filed: Sep. 17, 2010

(86) PCT No.: PCT/CN2010/001424
§ 371 (c)(1),
(2), (4) Date: Mar. 15, 2012

(87) PCT Pub. No.: WO2011/032361
PCT Pub. Date: Mar. 24, 2011

(65) Prior Publication Data
US 2012/0179060 A1 Jul. 12, 2012

(30) Foreign Application Priority Data
Sep. 17, 2009 (CN) .......................... 2009 1 0176499

(51) Int. Cl.
*A61B 5/0402* (2006.01)
*A61B 5/0404* (2006.01)
*A61B 5/00* (2006.01)

(52) U.S. Cl.
CPC ............... *A61B 5/0404* (2013.01); *A61B 5/742* (2013.01); *A61B 2560/0468* (2013.01)

(58) Field of Classification Search
CPC ....... A61B 5/06; A61B 5/0402; A61B 5/0432
USPC .......................................... 600/507, 509, 519
See application file for complete search history.

(56) References Cited

U.S. PATENT DOCUMENTS

| | | | |
|---|---|---|---|
| 6,605,046 B1 * | 8/2003 | Del Mar | 600/507 |
| 2003/0187363 A1 * | 10/2003 | Alroy | 600/509 |
| 2007/0142738 A1 | 6/2007 | Hung | |

FOREIGN PATENT DOCUMENTS

| | | |
|---|---|---|
| CN | 1419888 A | 5/2003 |
| CN | 1647754 A | 8/2005 |
| WO | 2009041127 A1 | 4/2009 |

* cited by examiner

*Primary Examiner* — Christopher D Koharski
*Assistant Examiner* — Michael D Abreu

(57) ABSTRACT

An ECG data acquisition device is provided, including a main housing, at least two electrodes, an ECG signal acquisition circuitry having a processor and a memory for storing acquired data, a connector for communication, and a movable housing, covering the connector and having at least an electrode mounted thereon, wherein as executing the ECG signal acquisition, the movable housing is in a first state, and as communicating with an external equipment, the movable housing is moved to a second state for exposing the connector and electrically disconnecting the electrode thereon from the ECG signal acquisition circuitry.

17 Claims, 7 Drawing Sheets

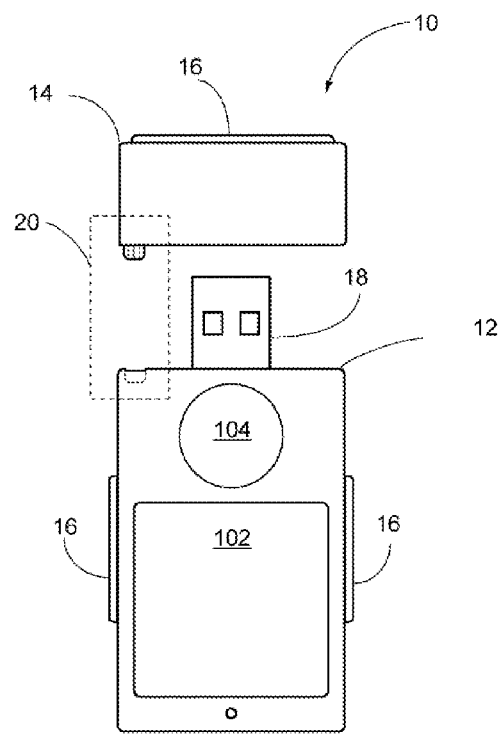
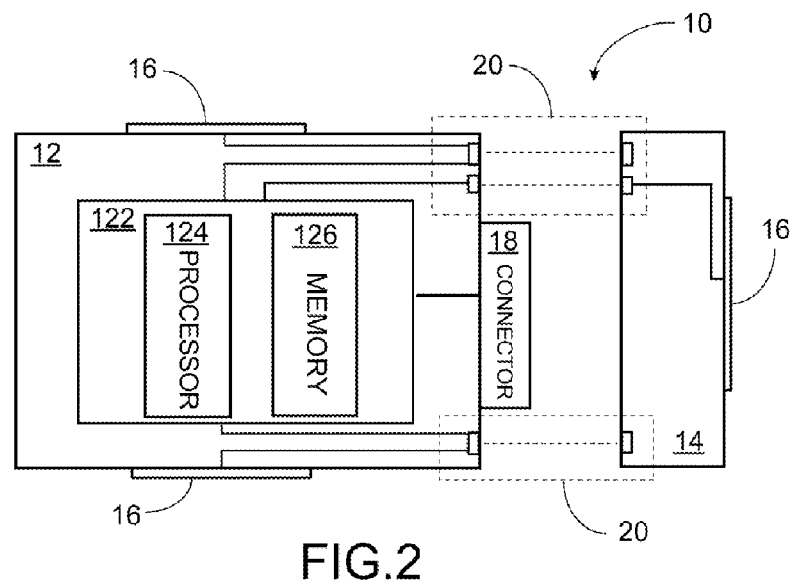

ECG SIGNAL ACQUISITION DEVICE

FIELD OF THE INVENTION

The present invention is related to an ECG signal acquisition device, and more particularly to an ECG signal acquisition device which can provide electrical isolation and safety as transmitting the acquired data.

BACKGROUND OF THE INVENTION

Generally, the portable ECG signal acquisition devices, such as, HCG-801 (a portable electrocardiometer produced by Omron, and SCS-H10/H20 (an electrocardiogram recording device manufactured by TOSHIBA), have their electrodes mounted on the surface, so that the electrodes can be contacted with the skin as performing the measurement.

It is common that the above-described portable ECG signal acquisition devices need to be connected with an external equipment, e.g., a personal computer, for configuration, signal/data output, and/or charging. To provide electric isolation of the device is an important issue if the external equipment is connected with the power distribution network, so as to protect not only the user but also the circuitries of the device and the equipment.

Then, if the electric isolation design can cooperate with a changeable mechanical structure related to an intuitive operation for connecting the device to the external equipment, then the electric safety should be further assured. Moreover, if it can be designed to associate the changeable mechanical structure with the built-in connector of the device, the operation convenience can be further improved since the extra transmission cable is no more needed.

Therefore, the object of the present invention is to provide an ECG signal acquisition device whose design for electric isolation can be achieved by an intuitive changing of the mechanical structure.

Another object of the present invention is to provide an ECG signal acquisition device with a movable housing, whose position, in accordance with different operation modes, can be varied to decide the conduction state of the data acquisition circuitry, thereby achieving the electric isolation as connecting with the external equipment.

A further object of the present invention is to provide an ECG signal acquisition device which is furnished with a built-in connector for communication with the external equipment, so that the device configuration, data/signal output and/or charging can be performed without an extra transmission cable.

SUMMARY OF THE INVENTION

In an aspect of the present invention, an ECG signal acquisition device is provided, including a main housing, at least two electrodes, an ECG signal acquisition circuitry having a processor and a memory for storing acquired data, a connector for communication, and a movable housing, covering the connector and having at least an electrode mounted thereon, wherein as executing the ECG signal acquisition, the movable housing is in a first position in relation to the main housing, and as communicating with an external equipment, the movable housing is moved to a second position in relation to the main housing for exposing the connector and electrically disconnecting the electrode thereon from the ECG signal acquisition circuitry.

Therefore, by changing the movable housing to decide the conduction state of the electrodes, the ECG signal acquisition device according to the present invention can provide the electric isolation in a more intuitive way. And, owing to the built-in connector, the inconvenience to use the cable for data transmission also can be eliminated.

Here, the first position indicates that the movable housing is integrated with the main housing to form an entity and the device is capable of performing the ECG signal acquisition. The second position indicates that the connector is exposed, in which the movable housing can be completely separated from or still linked with the main housing, without limitation.

In another aspect of the present invention, on the other hand, it is possible to design the movable housing without the electrodes mounted thereon. For example, the position of the movable housing can be related to the on/off of a switch, such as a tact switch, which decides the conduction of the circuitry for ECG signal acquisition, or it also can be that the circuitry is extended to the movable housing to achieve the electric disconnection. Therefore, the arrangement can be varied without limitation.

In a preferred embodiment, the quantity of the movable housing can be implemented to be plural, each of which respectively has the electrode(s) of different positions, quantities and types. Thus, through exchanging the movable housing, the ECG signal acquisition device can obtain different electrode arrangements, such as, to increase the amount of electrodes, to change from a dry electrode to a wet gel electrode, and/or to replace the original electrodes, so as to perform different kinds of ECG signal acquisitions in accordance with various measurement purposes. Alternatively, the movable housing also can be connected with at least a sensor, e.g., an oximeter, to cooperate with the ECG signal acquisition, without limitation. Particularly, the movable housing can further contain therein the circuitry corresponding to the electrode(s)/sensor(s) connected thereto, so as to support the additional measurement(s).

Advantageously, the electrodes can be all mounted on the surface of the device to provide a handheld operation, or a portion of the electrodes can be connected via lead-wires. And, an extension portion can be further provided to connect with at least an additional electrode/sensor, so as to widen the application range of the device.

Consequently, the present invention provides an enhanced design to assure the electric isolation in an ECG signal acquisition device. First, a movable housing is provided to decide the electrical conduction of the electrodes by changing the position thereof in relation to the main housing, and then, a built-in connector for performing data/signal output and/or device configuration is covered by the movable housing to further ensure the safety. Accordingly, the additional benefit will be the need of the extra transmission cable can be eliminated. Furthermore, by providing plural movable housings, the electrode deployment can be varied, and also, the function of the device also can be expanded.

BRIEF DESCRIPTION OF THE DRAWINGS

A more detailed understanding of the invention may be had from the following description of a preferred embodiment, given by way of example, and to be understood in conjunction with the accompanying drawings, wherein:

FIG. 1 is an appearance view showing an ECG signal acquisition device according to a first preferred embodiment of the present invention;

FIG. 2 is a schematic block diagram of the ECG signal acquisition device according to the first preferred embodiment of the present invention;

DETAILED DESCRIPTION OF THE PREFERRED EMBODIMENTS

Figure 3A:
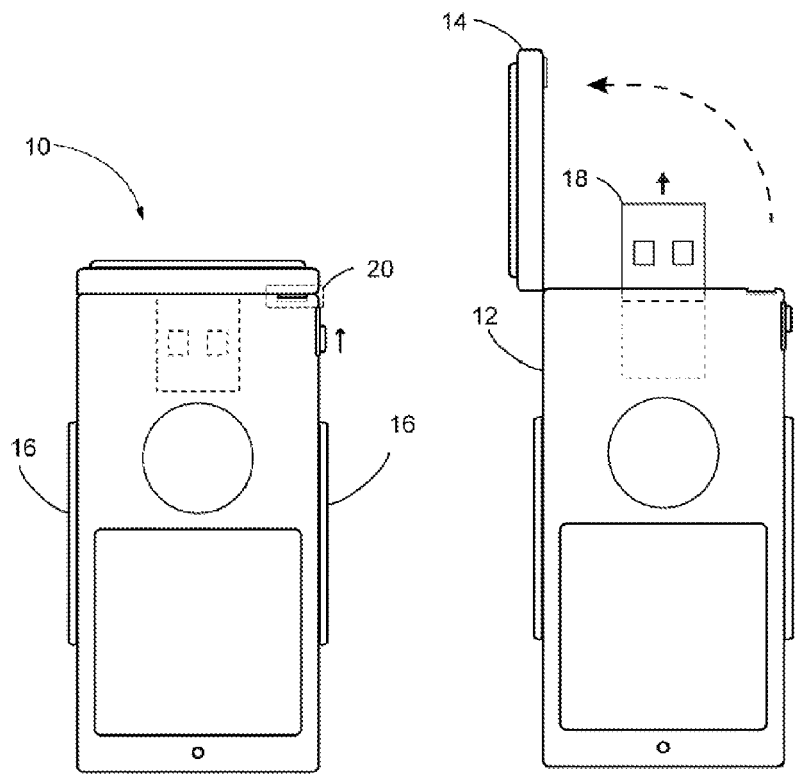
FIG. 3A~3C are schematic views showing exemplary ECG signal acquisition devices according to the first preferred embodiment of the present invention.

The present invention is to utilize the concept that a connector is necessary for the ECG signal acquisition device to perform data/signal transmission and/or device configuration, so that if a cover of the connector can be designed to decide the electrical conduction of the electrodes, then the electric isolation and safety for protecting the user and the circuitry of the device can be achieved in a more institutive way. On the other hand, if the connector can be a built-in connector, the need of the transmission cable can further be omitted. Accordingly, the present invention is related to an ECG signal acquisition device whose electric isolation is designed to associate with obtaining a built-in connector.

Please refer to FIG. 1 and FIG. 2 which respectively an appearance view and a schematic block diagram showing an ECG signal acquisition device according to a first preferred embodiment of the present invention. The ECG signal acquisition device 10 includes a main housing 12 and a movable housing 14, and multiple electrodes 16 are respectively located on the main housing 12 and the movable housing 14 and also electrically connected to an ECG signal acquisition circuitry 122.

Here, the ECG signal acquisition circuitry 122 can include, but not limited, a processor, an analog signal processing module, an analog/digital (A/D) converter, and a memory, so as to perform all kinds of processes, such as, filtering, amplification, digitization, calculation, analysis, interpretation, and storage. Because these are the basics for physiological signal processing, the accompanying drawings only illustrate the processor 124 and the memory 126 which are related to the descriptions, and others are omitted for simplification.

It should be noted that although the electrodes 16 illustrated in FIG. 1 are implemented to mount on the surfaces of the housings 12, 14, the electrodes also can be connected via wires, such as, cup electrodes, wet gel electrodes and handheld electrodes, without limitation.

Moreover, the ECG signal acquisition device 10 of the present invention is also furnished with a connector 18. The connector 18 is connected to the ECG signal acquisition circuitry 122 and is responsible for the communication with an external equipment. Here, particularly, as shown in FIG. 1, the connector 18 is covered by the movable housing 14.

Generally, a physiological signal acquisition device may possess a connection port, and, for performing device configuration and/or data/signal transmission, the connection port should cooperate with a transmission cable to connect with the external equipment, e.g., a personal computer. Different from the conventional situations, in the present invention, the connector 18 is built in the ECG signal acquisition device 10 and covered by the movable housing 14, so that when there is the need to connect to the external equipment, the connector 18 can be uncovered and directly used without the cable.

In this embodiment, because the ECG signal acquisition device 10 performs the communication mainly via the connector 18 and at least an electrode 16 is mounted on the movable housing 14, the electric isolation can be naturally achieved as the user detaches the movable housing 14 to utilize the connector 18. That is, the electric conduction of the electrodes 16 and the ECG signal acquisition circuitry 122 can be decided by if the movable housing 14 is integrated with the main housing 12.

Accordingly, the movable housing 14 of the present invention is implemented to have two positions in relation to the main housing. First, as the ECG signal acquisition is performed, the movable housing 14 is in a first position for integrating with the main housing 12 to form an entity, so that not only the electrode 16 thereon is located at a position capable of performing the ECG signal acquisition, but the ECG signal acquisition circuitry 122 is also electrically conducted and ready for ECG signal acquisition. Then, when there is the need to utilize the connector 18, the movable housing 14 is moved to a second position to uncover the connector 18, such that the electrode 16 and the ECG signal acquisition circuitry 122 can be electrically disconnected thereby.

Figure 3B:
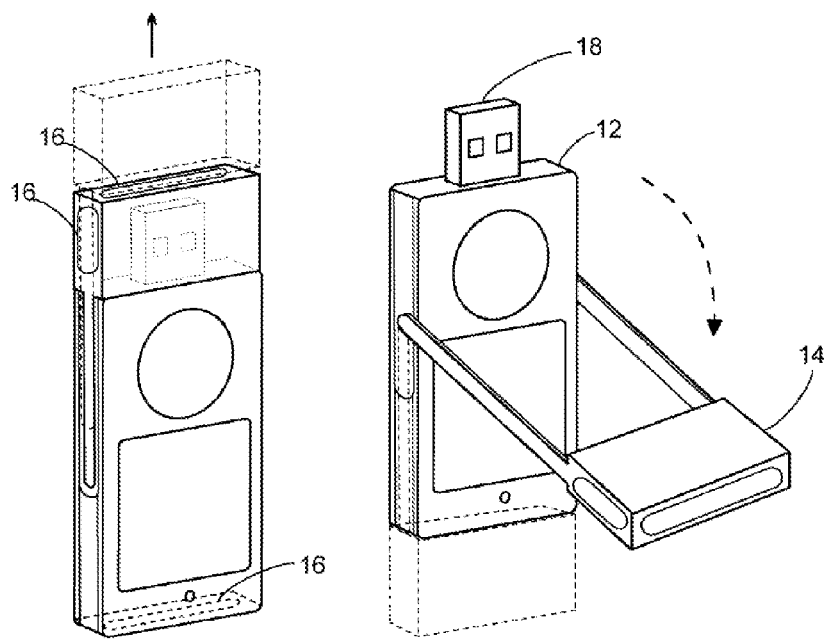

Here, it can be implemented that the movable housing 14 and the main housing 12 are completely separated (as shown in FIG. 1), or disengaged but still linked (as shown in FIG. 3A and FIG. 3B), without limitation. That is, the point is to expose the connector and electrically disconnect the circuitry, and the method for achieving this is not restricted.

As to the connector 18, it can be, but not limited, USB, 1394, UART or other connectors commonly used for data/signal transmission, and should be correspondingly matched to the communication port of the external equipment. Further, in addition to the communication, the connector 18 also can be used for charging, such as, the USB connector. Or, alternatively, the ECG signal acquisition device 10 can additionally possess a charging port (not shown) that also covered by the movable housing 14, so as to provide the electric protection.

Figure 3C:
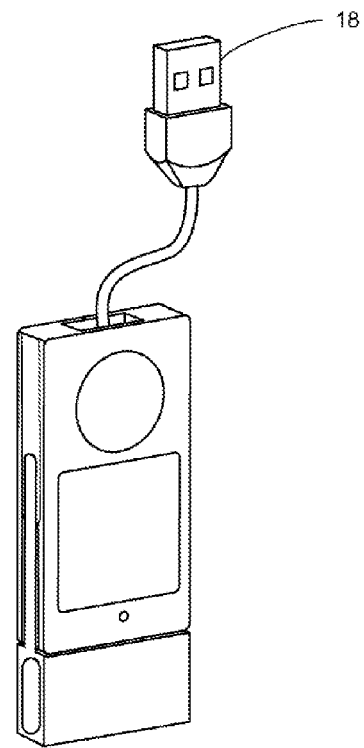

Moreover, the implementations of the movable housing 14 and the connector 18 can be varied in accordance with different demands. For example, the movable housing can be a lid (as shown in FIG. 1) completely separable from the main housing 12, a lid hinged on the main housing 12 (as shown in FIG. 3A), or a cover which can be slid and turned to expose the connector 18 (FIG. 3B). On the other hand, the connector 18 can be implemented to have a fixed position (FIG. 1), be pushed out as the movable housing is moved (FIG. 3A), be manually pulled out by the user after the movable housing 14 is moved away (FIG. 3C), or be ejected by pressing a button/switch (FIG. 5C). Therefore, the implementations of the movable housing and the connector are not limited.

Here, for utilizing the movable housing 14 to decide the conduction state of the electrodes 16 and the ECG signal acquisition circuitry 122, a corresponding pair of electrical connection structures 20 are respectively provided in the movable housing 14 and the main housing 12. For example, it can utilize pins (FIG. 1), sheet metals (FIG. 3A), or even a connector (FIG. 5C) to achieve the electrical connection. Besides, the corresponding electrical connection structures 20 also can be directly mounted between two housings at the positions where the mechanical integration is performed. For example, the fastener structures, or the corresponding engagement structures (such as the sliding structures between the main housing and the movable housing shown in FIG. 3B). Hence, the main purpose is to achieve the electrical connection therebetween, without limitation.

Furthermore, the ECG signal acquisition device according to the present invention also can be provided with a wireless communication module in addition to the connector 18, so that during the ECG signal acquisition, the data/signals can further be transmitted to the external equipment in real time for monitoring and/or storage.

The ECG signal acquisition device 10 can be further provided with a display 102, such as, a LED or LCD, for showing the related information during/after the ECG signal acquisition, and an operation interface 104 for facilitating the user to perform the ECG signal acquisition. Plus, the memory 126 can be implemented to be removable, so that, in addition to performing data/signal transmission, the storage capacity also can be upgraded. Particularly, the slot for the removable memory also can be covered by the movable housing for safety.

Besides, the quantity of electrodes also can be increased. For example, the reference electrode and/or ground electrode can be added to improve the accuracy, and/or more electrodes can be added to achieve the multi-lead ECG measurement or to provide different operation modes e.g., different holding manners. Hence, there is no limitation.

Figure 4A:
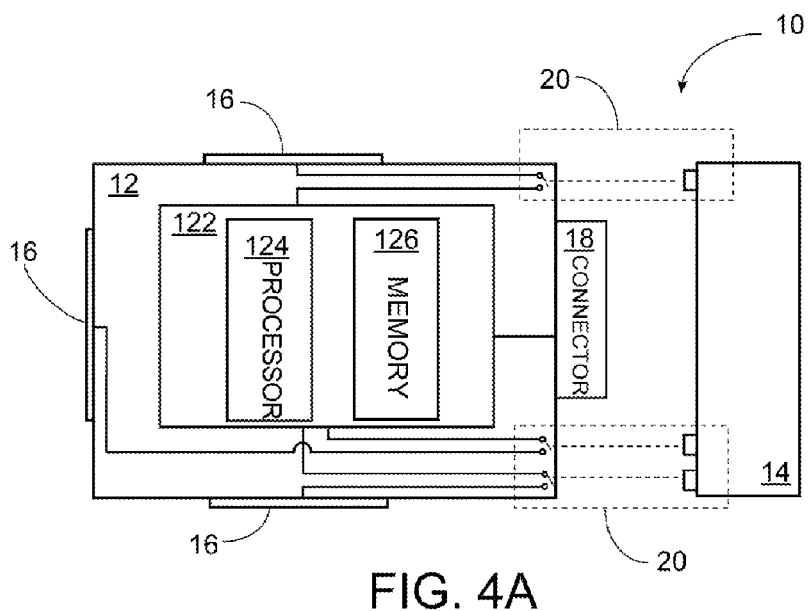
FIGS. 4A~4C are schematic block diagrams views of the ECG signal acquisition devices according to a second preferred embodiment of the present invention.
Figure 4B:
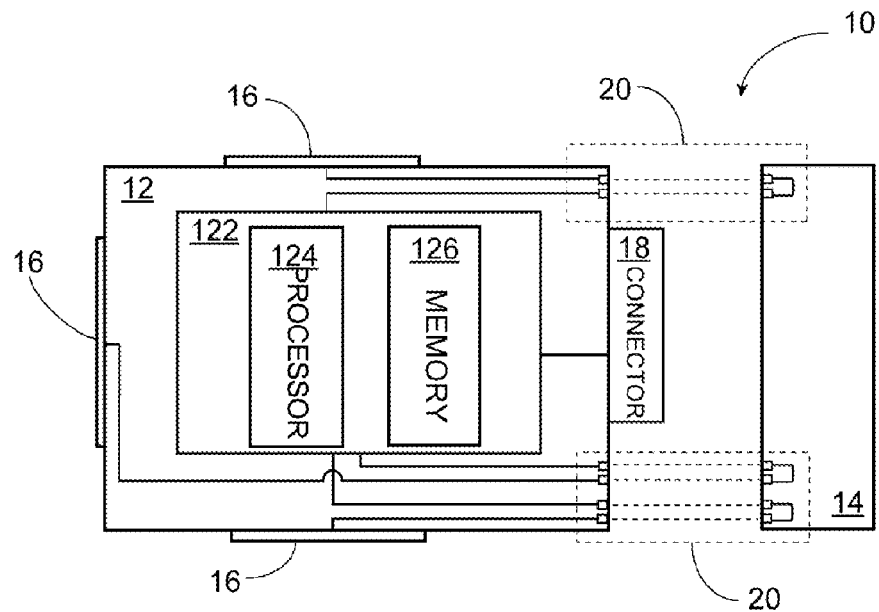
Figure 4C:
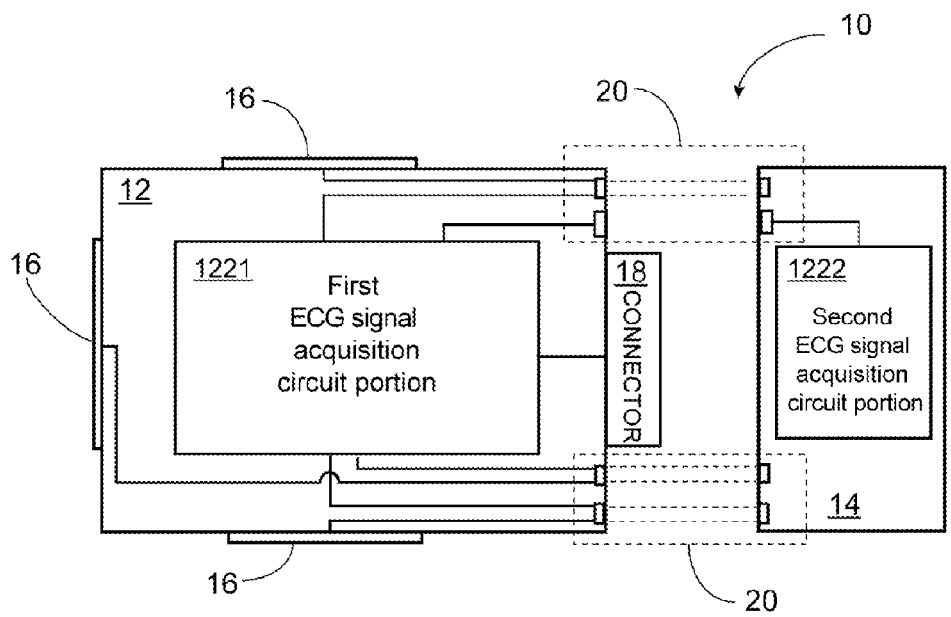

Then, please refer to FIGS. 4A~4C, which are schematic block diagrams showing the exemplary ECG signal acquisition devices according to a second preferred embodiment of the present invention, in which the movable housing 14 is implemented to not include the electrode 16. In this embodiment, although the electrode is not mounted on the movable housing, the electric conduction of the electrodes on the main housing 12 and the ECG signal acquisition circuitry 122 still can be decided thereby. That is, when the movable housing 14 is separated from the main housing 12 and moved to the second position, the electric isolation still can be achieved thereby.

The method to achieve the electrical disconnection, namely, the corresponding electrical connection structures 20, can have many choices. For example, as shown in FIG. 4A, a switch, whose on/off is respectively corresponding to the separation and the combination between the movable housing 14 and the main housing 12, can be located in the circuit loop, so as to control the conduction state of the loop. Or, as shown in FIG. 4B, it also can be the loop is extended into the movable housing 14, so that the electric disconnection can be naturally achieved as the housing 14 is moved to the second position. Or, further, as shown in FIG. 4C, the ECG signal acquisition circuitry 122 can be divided into two portions, a first ECG signal acquisition circuit portion 1221 and a second ECG signal acquisition circuit portion 1222, for being respectively placed in the two housings 12, 14, for example, to locate the analog signal processing module in the movable housing 14 and other electrical components in the main housing 12. Thus, there is no limitation.

Here, it should be noted that these electric disconnection methods also can be applied to the embodiment shown in FIG. 2, and it only needs to pay attention to the connection of the electrode mounted on the movable housing 14.

In another preferred embodiment, the quantity of the movable housing can be implemented to be plural, that is, the movable housing is designed to be exchangeable. By providing different movable housings to respectively combine with the main housing, not only the deployment of electrodes can be altered, the function of the device also can be updated. For example, the type, position and/or quantity of the electrodes 16 can be varied, and/or additional electrode(s) and/or at least a sensor can be employed to cooperate or replace the original electrode(s). Preferably, the movable housing 14 also can contain therein circuitry corresponding to the electrode(s)/sensor(s) connected thereto. Since the device 10 is mainly for ECG signal acquisition, the original circuitry might not be able to support the additional measurement(s), so that through exchanging the movable housing 14, the related circuitry can be added thereto. For example, the movable housing can be implemented to connect an oximerter, and the movable housing can accordingly contain the related circuitry therein. Thus, the function of the device 10 can be expanded without limitation.

Figure 5A:
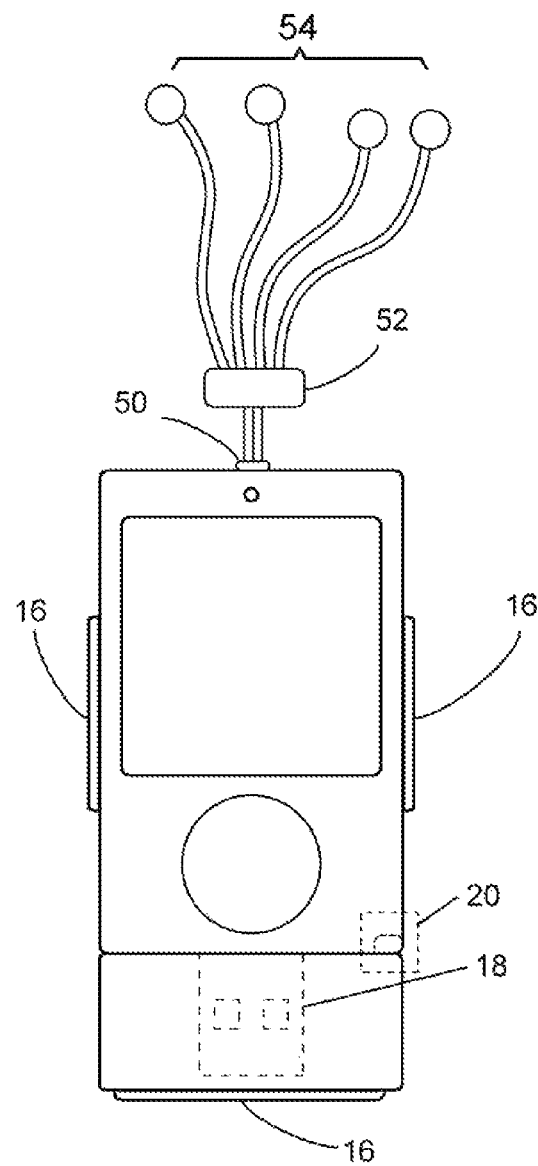
FIGS. 5A~5C are schematic views showing exemplary ECG signal acquisition devices according to the second preferred embodiment of the present invention
Figure 5B:
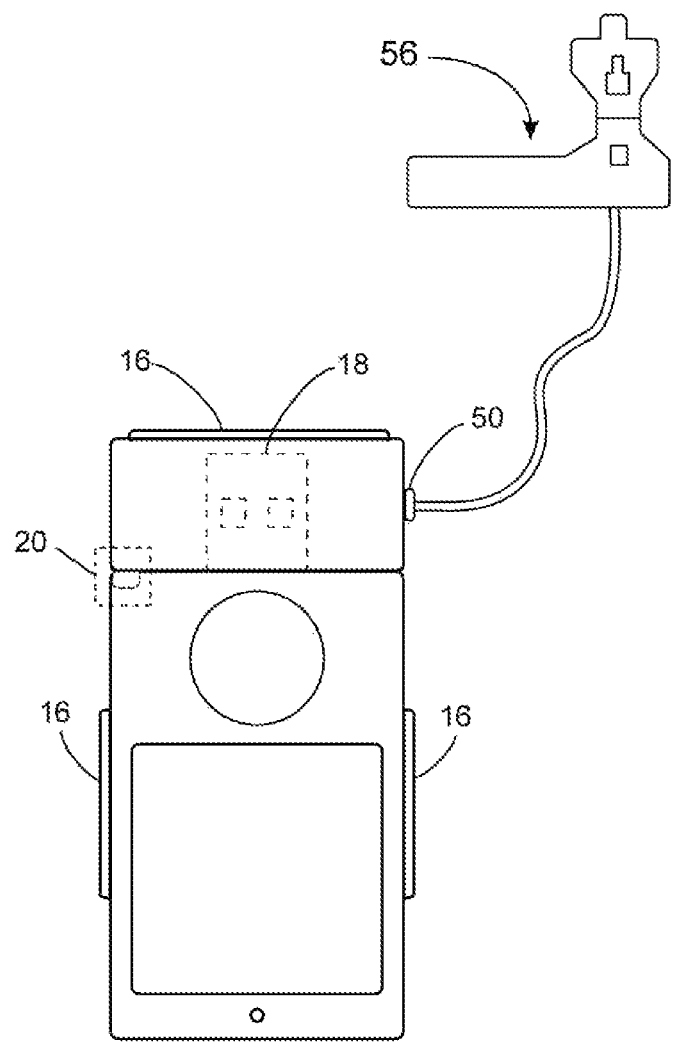
Figure 5C:
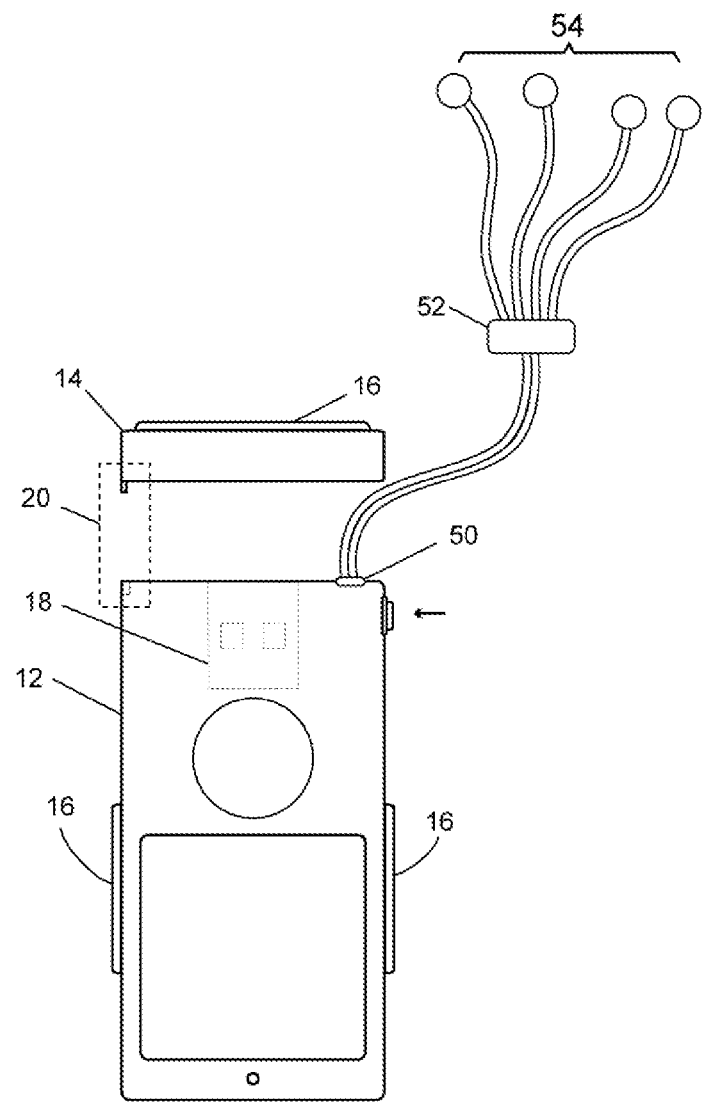

Furthermore, the ECG signal acquisition device 10 according to the present invention also can further include an extension port 50 for additionally connecting to at least an electrode/sensor, as shown in FIG. 5A, and even, a junction box 52 can be employed to manage a larger amount of electrodes 54. Then, FIG. 5B shows that the extension port 50 is located on the movable housing 14, and as described above, the circuit contained therein can be varied in accordance with the connected electrode(s)/sensor(s), e.g., an oximeter 56. Alternatively, the extension port 50 also can be covered by the movable housing 14, as shown in FIG. 5C, and this will be more suitable for the situation that the connector 18 is pulled (FIG. 3B) or pushed out, in which it can be designed that the ECG signal acquisition circuitry 122 will be electrically conducted as the extension port 50 is used. Hence, there is no limitation.

In the aforesaid, the present invention achieves the electric isolation for an ECG signal acquisition device by utilizing a movable housing which can decide the electric conduction of the electrodes. And, because the built-in connector for communication, e.g., data/signal output, device configuration and charging, is covered by the movable housing, the electric safety can be further ensured, and additionally, the need of the extra transmission cable also can be omitted. Besides, through providing plural movable housings of different requirements, it provides the possibility to alter the arrangement of the electrodes and also to expand the function of the device.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. An ECG signal acquisition device, comprising:
   at least two electrodes;
   a main housing, having at least one electrode mounted on a surface thereof for being contacted by a user;
   an ECG signal acquisition circuitry, comprising:
     a processor; and
     a memory, for storing acquired data;
   a connector for communication and charging; and
   a movable housing, covering the connector and having at least one electrode mounted thereon, wherein the movable housing is capable of being moved by the user to a first position in relation to the main housing or a second position in relation to the main housing,
   wherein
   when the movable housing is moved to the first position in relation to the main housing, the electrode on the main housing is electrically connected to the ECG signal acquisition circuitry for allowing ECG signal acquisition; and
   when the movable housing is moved to the second position in relation to the main housing, the connector is exposed for allowing communication and charging, and for electrically disconnecting the electrode on the main housing from the ECG signal acquisition circuitry, so as to achieve an electric isolation of the ECG signal acquisition device.

2. The device as claimed in claim 1, further comprising at least an extension port for connecting with at least a sensor/electrode.

3. The device as claimed in claim 2, wherein the extension port is located on the movable housing.

4. The device as claimed in claim 1, wherein the quantity of the movable housing is implemented to be plural.

5. The device as claimed in claim 4, wherein different movable housings provide different types of electrodes.

6. The device as claimed in claim 1, wherein a portion of the ECG signal acquisition circuitry is contained in the movable housing.

7. The device as claimed in claim 1, wherein as in the first position in relation to the main housing, the movable housing and the main housing are integrated together to form an entity.

8. The device as claimed in claim 1, wherein as in the second position in relation to the main housing, the movable housing is completely separated from the main housing.

9. The device as claimed in claim 1, wherein as in the second position in relation to the main housing, the connector is uncovered and the movable housing remains linked with the main housing.

10. The device as claimed in claim 1, wherein the connector is an USB, 1394 or UART connector.

11. The device as claimed in claim 1, further comprising a charging port covered by the movable housing.

12. The device as claimed in claim 1, further comprising a wireless communication module.

13. The device as claimed in claim 1, further comprising a display to show related information.

14. The device as claimed in claim 1, wherein the memory is removable.

15. An ECG signal acquisition device, comprising:
at least two electrodes;
a main housing, having at least one electrode mounted on a surface thereof for being contacted by a user;
an ECG signal acquisition circuitry, comprising:
    a processor; and
    a memory, for storing acquired data;
a connector for communication and charging; and
a movable housing, covering the connector and having a portion of the ECG signal acquisition circuitry disposed therein, wherein the movable housing is capable of being moved by the user to a first position in relation to the main housing or a second position in relation to the main housing,
wherein
when the movable housing is moved to the first position in relation to the main housing, the electrode on the main housing is electrically connected to the ECG signal acquisition circuitry for allowing ECG signal acquisition; and
when the movable housing is moved to the second position in relation to the main housing, the connector is exposed for allowing communication and charging, and for electrically disconnecting the electrode on the main housing from the ECG signal acquisition circuitry, so as to achieve an electric isolation of the ECG signal acquisition device.

16. The device as claimed in claim 15, wherein at least one of the electrodes is mounted on the surface of the main housing.

17. The device as claimed in claim 15, wherein at least one of the electrodes is extended out of the main housing by a wire.

* * * * *